(12) United States Patent
Sachs et al.

(10) Patent No.: US 12,262,922 B2
(45) Date of Patent: *Apr. 1, 2025

(54) MEDICAL DEVICE AND METHOD TO CORRECT DEFORMITY

(71) Applicant: K2M, Inc., Leesburg, VA (US)

(72) Inventors: Dan Sachs, Minneapolis, MN (US); Corbett Stone, San Diego, CA (US)

(73) Assignee: K2M, Inc., Leesburg, VA (US)

( * ) Notice: Subject to any disclaimer, the term of this patent is extended or adjusted under 35 U.S.C. 154(b) by 396 days.

This patent is subject to a terminal disclaimer.

(21) Appl. No.: 17/668,955

(22) Filed: Feb. 10, 2022

(65) Prior Publication Data

US 2022/0160403 A1    May 26, 2022

Related U.S. Application Data

(63) Continuation of application No. 16/565,994, filed on Sep. 10, 2019, now Pat. No. 11,246,628, which is a (Continued)

(51) Int. Cl.
*A61B 17/70* (2006.01)
*A61B 17/00* (2006.01)
*A61B 17/56* (2006.01)

(52) U.S. Cl.
CPC ...... *A61B 17/7041* (2013.01); *A61B 17/7053* (2013.01); *A61B 17/707* (2013.01);
(Continued)

(58) Field of Classification Search
CPC ............ A61B 17/7041; A61B 17/7053; A61B 17/7052; A61B 17/66
See application file for complete search history.

(56) References Cited

U.S. PATENT DOCUMENTS 2,774,350 A    12/1956    Cleveland, Jr.
3,242,922 A    3/1966    Thomas
(Continued)

FOREIGN PATENT DOCUMENTS

DE    2644735 A1    4/1977
DE    2845647 A1    5/1980
(Continued)

OTHER PUBLICATIONS

Berry, James L. et al., A Morphometric Study of Human Lumbar and Selected Thoracic Vertebrae, 12 SPINE 362 (1987).
(Continued)

*Primary Examiner* — Julianna N Harvey
(74) *Attorney, Agent, or Firm* — Lerner David LLP

(57) ABSTRACT

A system for correcting a spinal deformity includes an implant fixed to one side of a vertebra and a rod extending along an axis of the spine on a second side of the vertebra. An adjustment member, which may include a reel, is coupled to the rod. A force directing member, such as a cable, extends between the rod and the adjustment member. The force directing member is retractable toward and extendible from the adjustment member. A method of correcting spinal deformity includes providing an implant, a rod, an adjustment member coupled to the rod, and a force directing member extending between the rod and the adjustment member. The adjustment member can be retractable toward and extendible from the adjustment member.

26 Claims, 15 Drawing Sheets

Related U.S. Application Data continuation of application No. 15/817,750, filed on Nov. 20, 2017, now Pat. No. 10,426,523, which is a continuation of application No. 14/628,573, filed on Feb. 23, 2015, now Pat. No. 9,848,917, which is a continuation of application No. 13/446,950, filed on Apr. 13, 2012, now abandoned, which is a continuation of application No. 12/134,058, filed on Jun. 5, 2008, now Pat. No. 8,162,979.

(60) Provisional application No. 60/933,326, filed on Jun. 6, 2007.

(52) U.S. Cl.
CPC ............. *A61B 2017/00017* (2013.01); *A61B 2017/00212* (2013.01); *A61B 2017/00221* (2013.01); *A61B 2017/564* (2013.01)

(56) References Cited

U.S. PATENT DOCUMENTS

| | | |
|---|---|---|
| 3,352,226 A | 11/1967 | Nelsen |
| 3,648,691 A | 3/1972 | Lumb et al. |
| 3,693,616 A | 9/1972 | Roaf et al. |
| 3,865,105 A | 2/1975 | Lode |
| 4,024,588 A | 5/1977 | Janssen et al. |
| 4,078,559 A * | 3/1978 | Nissinen ............ A61B 17/7053 606/263 |
| 4,269,178 A | 5/1981 | Keene |
| 4,274,401 A | 6/1981 | Miskew |
| 4,355,645 A | 10/1982 | Mitani et al. |
| 4,361,141 A | 11/1982 | Tanner |
| 4,369,769 A | 1/1983 | Edwards |
| 4,404,967 A | 9/1983 | Bacal et al. |
| 4,411,259 A | 10/1983 | Drummond |
| 4,411,545 A | 10/1983 | Roberge |
| 4,448,191 A | 5/1984 | Rodnyansky et al. |
| 4,505,268 A | 3/1985 | Sgandurra |
| 4,554,914 A | 11/1985 | Kapp et al. |
| 4,573,454 A | 3/1986 | Hoffman |
| 4,604,995 A | 8/1986 | Stephens et al. |
| 4,611,581 A | 9/1986 | Steffee |
| 4,611,582 A | 9/1986 | Duff |
| 4,648,388 A | 3/1987 | Steffee |
| 4,653,481 A | 3/1987 | Howland et al. |
| 4,697,582 A | 10/1987 | William |
| 4,738,251 A | 4/1988 | Plaza |
| 4,773,402 A | 9/1988 | Asher et al. |
| 4,805,602 A | 2/1989 | Puno et al. |
| 4,815,453 A | 3/1989 | Cotrel |
| 4,827,918 A | 5/1989 | Olerud |
| 4,854,311 A | 8/1989 | Steffee |
| 4,936,848 A | 6/1990 | Bagby |
| 5,000,166 A | 3/1991 | Karpf |
| 5,005,562 A | 4/1991 | Cotrel |
| 5,011,484 A | 4/1991 | Breard |
| 5,030,220 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,127,912 A | 7/1992 | Ray et al. |
| 5,129,900 A | 7/1992 | Asher et al. |
| 5,133,716 A | 7/1992 | Plaza |
| 5,147,363 A | 9/1992 | Harle |
| 5,176,679 A | 1/1993 | Lin |
| 5,176,680 A | 1/1993 | Vignaud et al. |
| 5,181,917 A | 1/1993 | Rogozinski |
| 5,190,543 A | 3/1993 | Schlapfer |
| 5,196,014 A | 3/1993 | Lin |
| 5,207,678 A | 5/1993 | Harms et al. |
| 5,209,752 A | 5/1993 | Ashman et al. |
| 5,219,349 A | 6/1993 | Krag et al. |
| 5,242,443 A | 9/1993 | Kambin |
| 5,254,118 A | 10/1993 | Mirkovic |
| 5,257,994 A | 11/1993 | Lin |
| 5,259,398 A | 11/1993 | Vrespa |
| 5,282,862 A | 2/1994 | Baker et al. |
| 5,306,275 A | 4/1994 | Bryan |
| 5,312,404 A | 5/1994 | Asher et al. |
| 5,312,410 A | 5/1994 | Miller et al. |
| 5,330,474 A | 7/1994 | Lin |
| 5,352,226 A | 10/1994 | Lin |
| 5,366,455 A | 11/1994 | Dove et al. |
| 5,368,594 A | 11/1994 | Martin et al. |
| 5,380,323 A | 1/1995 | Howland |
| 5,380,325 A | 1/1995 | Lahille et al. |
| 5,382,248 A | 1/1995 | Jacobson et al. |
| 5,387,212 A | 2/1995 | Yuan et al. |
| 5,387,213 A | 2/1995 | Breard et al. |
| 5,391,168 A | 2/1995 | Sanders et al. |
| 5,397,363 A | 3/1995 | Gelbard |
| 5,413,576 A | 5/1995 | Rivard |
| 5,436,542 A | 7/1995 | Petelin et al. |
| 5,437,669 A | 8/1995 | Yuan et al. |
| 5,437,671 A * | 8/1995 | Lozier ................ A61B 17/7043 606/252 |
| 5,456,722 A | 10/1995 | McLeod et al. |
| 5,470,333 A | 11/1995 | Ray |
| 5,480,440 A | 1/1996 | Kambin |
| 5,486,174 A | 1/1996 | Fournet-Fayard et al. |
| 5,487,744 A | 1/1996 | Howland |
| 5,490,851 A | 2/1996 | Nenov et al. |
| 5,496,318 A | 3/1996 | Howland et al. |
| 5,498,262 A | 3/1996 | Bryan |
| 5,501,684 A | 3/1996 | Schlapfer et al. |
| 5,520,688 A | 5/1996 | Lin |
| 5,540,689 A | 7/1996 | Sanders et al. |
| 5,544,993 A | 8/1996 | Harle |
| 5,549,679 A | 8/1996 | Kuslich |
| 5,562,660 A | 10/1996 | Grob |
| 5,562,662 A | 10/1996 | Brumfield et al. |
| 5,569,246 A | 10/1996 | Ojima et al. |
| 5,571,191 A | 11/1996 | Filz |
| 5,584,626 A | 12/1996 | Assmundson |
| 5,586,983 A | 12/1996 | Sanders et al. |
| 5,591,165 A | 1/1997 | Jackson |
| 5,611,800 A | 3/1997 | Davis et al. |
| 5,643,259 A | 7/1997 | Sasso et al. |
| 5,645,599 A | 7/1997 | Samani |
| 5,649,926 A | 7/1997 | Howland |
| 5,658,284 A | 8/1997 | Sebastian et al. |
| 5,672,175 A | 9/1997 | Martin |
| 5,676,703 A | 10/1997 | Gelbard |
| 5,702,395 A | 12/1997 | Hopf |
| 5,702,399 A | 12/1997 | Kilpela et al. |
| 5,702,452 A | 12/1997 | Argenson et al. |
| 5,704,936 A | 1/1998 | Mazel |
| 5,713,898 A | 2/1998 | Stucker et al. |
| 5,725,582 A | 3/1998 | Bevan et al. |
| 5,728,097 A | 3/1998 | Mathews |
| 5,733,284 A | 3/1998 | Martin |
| 5,735,852 A | 4/1998 | Amrein et al. |
| 5,782,831 A | 7/1998 | Sherman et al. |
| 5,797,910 A | 8/1998 | Martin |
| 5,810,817 A | 9/1998 | Roussouly et al. |
| 5,810,819 A | 9/1998 | Errico et al. |
| 5,814,046 A | 9/1998 | Hopf et al. |
| 5,891,145 A | 4/1999 | Morrison et al. |
| 5,902,305 A | 5/1999 | Beger et al. |
| 5,910,142 A | 6/1999 | Tatar |
| 5,928,232 A | 7/1999 | Howland et al. |
| 5,938,663 A | 8/1999 | Petreto |
| 5,947,967 A | 9/1999 | Barker |
| 5,964,769 A | 10/1999 | Wagner et al. |
| 5,976,135 A | 11/1999 | Sherman et al. |
| 5,980,521 A | 11/1999 | Montague et al. |
| 5,984,924 A | 11/1999 | Asher et al. |
| 5,989,256 A | 11/1999 | Kuslich et al. |
| 6,015,409 A | 1/2000 | Jackson |
| 6,039,738 A | 3/2000 | Sanders et al. |
| 6,053,921 A | 4/2000 | Wagner et al. |
| 6,077,268 A | 6/2000 | Farris et al. |

(56) References Cited

U.S. PATENT DOCUMENTS

| | | | |
|---|---|---|---|
| 6,080,156 A | 6/2000 | Asher et al. |
| 6,086,590 A | 7/2000 | Margulies et al. |
| 6,123,706 A | 9/2000 | Lange |
| 6,132,431 A | 10/2000 | Nilsson et al. |
| 6,132,464 A | 10/2000 | Martin |
| 6,136,000 A | 10/2000 | Louis et al. |
| 6,176,861 B1 | 1/2001 | Bernstein et al. |
| 6,231,575 B1 | 5/2001 | Krag |
| 6,248,106 B1 | 6/2001 | Ferree |
| 6,251,111 B1 | 6/2001 | Barker et al. |
| 6,261,288 B1 | 7/2001 | Jackson |
| 6,277,120 B1 | 8/2001 | Lawson |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,325,805 B1 | 12/2001 | Ogilvie et al. |
| 6,328,739 B1 | 12/2001 | Liu et al. |
| 6,358,254 B1 | 3/2002 | Anderson |
| 6,364,883 B1 | 4/2002 | Santilli |
| 6,364,885 B1 | 4/2002 | Kilpela et al. |
| 6,391,030 B1 | 5/2002 | Wagner et al. |
| 6,402,752 B2 | 6/2002 | Schaffler-Wachter et al. |
| 6,419,703 B1 | 7/2002 | Fallin et al. |
| 6,423,065 B2 | 7/2002 | Ferree |
| 6,451,019 B1 | 9/2002 | Zucherman et al. |
| 6,458,131 B1 | 10/2002 | Ray |
| 6,488,683 B2 | 12/2002 | Lieberman |
| 6,514,255 B1 | 2/2003 | Ferree |
| 6,520,962 B1 | 2/2003 | Taylor et al. |
| 6,537,276 B2 | 3/2003 | Metz-Stavenhagen |
| 6,547,789 B1 | 4/2003 | Ventre et al. |
| 6,551,320 B2 | 4/2003 | Lieberman |
| 6,554,831 B1 | 4/2003 | Rivard et al. |
| 6,562,038 B1 | 5/2003 | Morrison |
| 6,565,569 B1 | 5/2003 | Assaker et al. |
| 6,565,605 B2 | 5/2003 | Goble et al. |
| 6,569,164 B1 | 5/2003 | Assaker et al. |
| 6,579,292 B2 | 6/2003 | Taylor |
| 6,579,319 B2 | 6/2003 | Goble et al. |
| 6,582,433 B2 | 6/2003 | Yun |
| 6,589,243 B1 | 7/2003 | Viart et al. |
| 6,610,091 B1 | 8/2003 | Reiley |
| 6,616,669 B2 | 9/2003 | Ogilvie et al. |
| 6,623,484 B2 | 9/2003 | Betz et al. |
| 6,626,906 B1 | 9/2003 | Young |
| 6,626,909 B2 | 9/2003 | Chin |
| 6,641,585 B2 | 11/2003 | Sato et al. |
| 6,645,207 B2 | 11/2003 | Dixon et al. |
| 6,656,185 B2 | 12/2003 | Gleason et al. |
| 6,682,532 B2 | 1/2004 | Johnson et al. |
| 6,682,533 B1 | 1/2004 | Dinsdale et al. |
| 6,685,705 B1 | 2/2004 | Taylor |
| 6,689,133 B2 | 2/2004 | Morrison et al. |
| 6,709,435 B2 | 3/2004 | Lin |
| 6,755,828 B2 | 6/2004 | Shevtsov et al. |
| 6,773,437 B2 | 8/2004 | Ogilvie et al. |
| 6,802,844 B2 | 10/2004 | Ferree |
| 6,811,567 B2 | 11/2004 | Reiley |
| 6,835,207 B2 | 12/2004 | Zacouto et al. |
| 6,840,127 B2 | 1/2005 | Moran |
| 6,860,884 B2 | 3/2005 | Shirado et al. |
| 6,946,000 B2 | 9/2005 | Senegas et al. |
| 6,966,910 B2 | 11/2005 | Ritland |
| 6,966,930 B2 | 11/2005 | Armin et al. |
| 6,986,771 B2 | 1/2006 | Paul et al. |
| 7,018,379 B2 | 3/2006 | Drewry et al. |
| 7,029,475 B2 | 4/2006 | Panjabi |
| 7,048,736 B2 | 5/2006 | Robinson et al. |
| 7,074,237 B2 | 7/2006 | Goble et al. |
| 7,083,621 B2 | 8/2006 | Shaolian et al. |
| 7,087,056 B2 | 8/2006 | Vaughan |
| 7,104,992 B2 | 9/2006 | Bailey |
| RE39,325 E | 10/2006 | Bryan |
| 7,128,743 B2 | 10/2006 | Metz-Stavenhagen |
| 7,160,312 B2 | 1/2007 | Saadat |
| 7,220,262 B1 | 5/2007 | Hynes |
| 7,270,665 B2 | 9/2007 | Morrison et al. |
| 7,294,129 B2 | 11/2007 | Hawkins et al. |
| 7,316,684 B1 | 1/2008 | Baccelli et al. |
| 7,335,203 B2 | 2/2008 | Winslow et al. |
| 7,338,490 B2 | 3/2008 | Ogilvie et al. |
| 7,344,539 B2 | 3/2008 | Serhan et al. |
| 7,361,196 B2 | 4/2008 | Fallin et al. |
| 7,367,978 B2 | 5/2008 | Drewry et al. |
| 7,481,828 B2 | 1/2009 | Mazda et al. |
| 7,524,324 B2 | 4/2009 | Winslow et al. |
| 7,763,053 B2 | 7/2010 | Gordon |
| 7,819,902 B2 | 10/2010 | Abdelgany et al. |
| 7,976,568 B2 | 7/2011 | Cheung et al. |
| 8,162,979 B2 | 4/2012 | Sachs et al. |
| 9,848,917 B2 | 12/2017 | Sachs et al. |
| 10,426,523 B2 | 10/2019 | Sachs et al. |
| 2002/0055739 A1 | 5/2002 | Lieberman |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2003/0040746 A1 | 2/2003 | Mitchell et al. |
| 2003/0093117 A1* | 5/2003 | Saadat ............... A61B 18/1442 606/221 |
| 2003/0109881 A1 | 6/2003 | Shirado et al. |
| 2003/0153915 A1 | 8/2003 | Nekozuka et al. |
| 2003/0220643 A1 | 11/2003 | Ferree |
| 2004/0006391 A1 | 1/2004 | Reiley |
| 2004/0097931 A1 | 5/2004 | Mitchell |
| 2004/0106921 A1 | 6/2004 | Cheung et al. |
| 2004/0149065 A1* | 8/2004 | Moran ................. B25J 17/0266 74/490.04 |
| 2004/0167520 A1 | 8/2004 | Zucherman et al. |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0033291 A1 | 2/2005 | Ebara |
| 2005/0033295 A1 | 2/2005 | Wisnewski |
| 2005/0043797 A1 | 2/2005 | Lee |
| 2005/0049705 A1 | 3/2005 | Hale et al. |
| 2005/0055096 A1 | 3/2005 | Serhan et al. |
| 2005/0080420 A1 | 4/2005 | Farris et al. |
| 2005/0149030 A1 | 7/2005 | Serhan et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson-MacDonald et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2006/0036246 A1* | 2/2006 | Carl .................... A61B 17/7067 606/248 |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1* | 3/2006 | Gordon ............... A61B 17/7016 606/907 |
| 2006/0058790 A1 | 3/2006 | Carl et al. |
| 2006/0058792 A1* | 3/2006 | Hynes ................. A61B 17/8605 606/279 |
| 2006/0064091 A1 | 3/2006 | Ludwig et al. |
| 2006/0084996 A1 | 4/2006 | Metz-Stavenhagen |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0217712 A1 | 9/2006 | Mueller et al. |
| 2006/0241594 A1 | 10/2006 | McCarthy et al. |

(56) References Cited

U.S. PATENT DOCUMENTS

| | | |
|---|---|---|
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0293663 A1 | 12/2006 | Walkenhorst et al. |
| 2007/0005062 A1 | 1/2007 | Lange et al. |
| 2007/0055373 A1 | 3/2007 | Hudgins et al. |
| 2007/0073293 A1 | 3/2007 | Martz et al. |
| 2007/0083200 A1 | 4/2007 | Gittings et al. |
| 2007/0093814 A1 | 4/2007 | Callahan et al. |
| 2007/0161987 A1 | 7/2007 | Capote et al. |
| 2007/0161994 A1 | 7/2007 | Lowery et al. |
| 2007/0162002 A1 | 7/2007 | Tornier |
| 2007/0167947 A1 | 7/2007 | Gittings |
| 2007/0168035 A1 | 7/2007 | Koske |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1 | 10/2007 | Falahee |
| 2007/0238335 A1 | 10/2007 | Veldman et al. |
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0288011 A1 | 12/2007 | Logan |
| 2008/0015577 A1 | 1/2008 | Loeb |
| 2008/0021466 A1 | 1/2008 | Shadduck et al. |
| 2008/0021469 A1 | 1/2008 | Holt |
| 2008/0065069 A1 | 3/2008 | Betz et al. |
| 2008/0077143 A1 | 3/2008 | Shluzas |
| 2008/0097441 A1 | 4/2008 | Hayes et al. |
| 2008/0140202 A1 | 6/2008 | Allard et al. |
| 2008/0177326 A1 | 7/2008 | Thompson |
| 2008/0183209 A1 | 7/2008 | Robinson et al. |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0228227 A1 | 9/2008 | Brown et al. |
| 2008/0234737 A1 | 9/2008 | Boschert |
| 2008/0234739 A1 | 9/2008 | Hudgins et al. |
| 2008/0262546 A1 | 10/2008 | Calvosa et al. |
| 2008/0281361 A1* | 11/2008 | Vittur ............... A61B 17/7052 606/100 |
| 2008/0306535 A1 | 12/2008 | Winslow et al. |
| 2008/0306536 A1 | 12/2008 | Frigg et al. |
| 2009/0012565 A1 | 1/2009 | Sachs et al. |
| 2009/0018583 A1 | 1/2009 | Song et al. |
| 2009/0024166 A1 | 1/2009 | Carl et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0069849 A1 | 3/2009 | Oh et al. |
| 2009/0093820 A1 | 4/2009 | Trieu et al. |
| 2009/0099607 A1 | 4/2009 | Fallin et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0125062 A1 | 5/2009 | Arnin |
| 2009/0194206 A1 | 8/2009 | Jeon et al. |
| 2010/0249837 A1* | 9/2010 | Seme ............... A61B 17/707 606/279 |
| 2011/0054536 A1* | 3/2011 | Elsebaie ............ A61B 17/705 606/279 |
| 2013/0123853 A1* | 5/2013 | Seme ............... A61B 17/7052 606/279 |

FOREIGN PATENT DOCUMENTS

| | | |
|---|---|---|
| EP | 0418387 A1 | 3/1991 |
| EP | 1281361 A1 | 2/2003 |
| FR | 2697744 | 5/1994 |
| FR | 2736535 A1 | 1/1997 |
| FR | 2781359 A1 | 1/2000 |
| FR | 2801492 A1 | 6/2001 |
| FR | 2872021 A1 | 12/2005 |
| JP | 2005169064 A | 6/2005 |
| JP | 2006512936 A | 4/2006 |
| JP | 2008513126 A | 5/2008 |
| JP | 2009501571 A | 1/2009 |
| SU | 888968 A1 | 12/1981 |
| WO | 2006010844 A1 | 2/2006 |
| WO | 2006017641 A2 | 2/2006 |
| WO | 2006034013 A1 | 3/2006 |
| WO | 2007011815 A2 | 1/2007 |
| WO | 2007051924 A1 | 5/2007 |
| WO | 2008086467 A2 | 7/2008 |

OTHER PUBLICATIONS

Fujita, Masaru et al., A Biomechanical Analysis of Sublaminar and Subtransverse Process Fixation Using Metal Wires and Polyethylene Cables, 31 SPINE 2202 (2006).

Girardi, Federico P. et al., Safety and Sublaminar Wires with Isola Instrumentation for the Treatment of Idiopathic Scoliosis, 25 Spine 691 (2000).

Liljenqvist, Ulf R. et al., Analysis of Vertebral Morphology in Idiopathic Scoliosis with Use of Magnetic Resonance Imaging and Multiplanar Reconstruction, 84 J Bone Joint Surg Am. 359 (2002).

Molnar, Szabolcs et al., Ex Vivo and in Vitro Determination of the Axial Rotational Axis of the Human Thoracic Spine, 31 SPINE E984 (2006).

Rajasekaran S. et al., Eighteen-Level Analysis of Vertebral Rotation Following Harrington-Luque Instrumentation in Idiopathic Scoliosis, 76 J Bone Joint Surg Am. 104 (1994).

Wenger, Dennis R. et al., Biomechanics of Scoliosis Correction by Segmental Spinal Instrumentation, 7 Spine 260 (1982).

White III, Augustus A. et al., Biomechanics of the Spine 28-29, Tbl. 1-5 (2d ed. 1990).

International Search Report dated Oct. 2, 2008 for PCT/US2008/065979.

Supplementary European Search Report for Application No. EP08770234.6 dated Jan. 28, 2013, 2 pages.

* cited by examiner

MEDICAL DEVICE AND METHOD TO CORRECT DEFORMITY

CROSS-REFERENCE TO RELATED APPLICATIONS

The present application is a continuation of U.S. patent application Ser. No. 16/565,994, filed Sep. 10, 2019, which is a continuation of U.S. patent application Ser. No. 15/817,750, filed Nov. 20, 2017 now U.S. Pat. No. 10,426,523, which is a continuation of U.S. patent application Ser. No. 14/628,573, filed Feb. 23, 2015 now U.S. Pat. No. 9,848,917, which is a continuation of U.S. patent application Ser. No. 13/446,950, filed Apr. 13, 2012, which is a continuation of U.S. patent application Ser. No. 12/134,058, filed Jun. 5, 2008, now U.S. Pat. No. 8,162,979, which claims priority to U.S. Provisional Application Ser. No. 60/933,326, filed Jun. 6, 2007. The above-referenced applications are expressly incorporated herein by reference in their entireties.

BACKGROUND OF THE INVENTION

1. Field of the Invention

This application generally relates to devices and methods for adjusting anatomical structures. More particularly, this application related to devices and methods for correcting skeletal deformities, such as spinal deformities.

2. Description of the Related Art

Certain spine conditions, defects, deformities (e.g., scoliosis) as well as injuries may lead to structural instabilities, nerve or spinal cord damage, pain or other manifestations. Back pain (e.g., pain associated with the spinal column or mechanical back pain) may be caused by structural defects, by injuries or over the course of time from the aging process. For example, back pain is frequently caused by repetitive and/or high stress loads on or increased motion around certain boney or soft tissue structures. The natural course of aging leads to degeneration of the disc, loss of disc height, and instability of the spine among other structural manifestations at or around the spine. With disc degeneration, the posterior elements of the spine bear increased loads with disc height loss, and subsequently attempt to compensate with the formation of osteophytes and thickening of various stabilizing spinal ligaments. The facet joints may develop pain due to arthritic changes caused by increased loads. Furthermore, osteophytes in the neural foramina and thickening of spinal ligaments can lead to spinal stenosis, or impingement of nerve roots in the spinal canal or neural foramina. Scoliosis may also create disproportionate loading on various elements of the spine and may require correction, stabilization or fusion.

Pain caused by abnormal motion of the spine has long been treated by fixation of the motion segment. Spinal fusion is one way of stabilizing the spine to reduce pain. In general, it is believed that anterior interbody or posterior fusion prevents movement between one or more joints where pain is occurring from irritating motion. Fusion typically involves removal of the native disc, packing bone graft material into the resulting intervertebral space, and anterior stabilization, e.g., with intervertebral fusion cages or posterior stabilization, e.g., supporting the spinal column with internal fixation devices such as rods and screws. Internal fixation is typically an adjunct to attain intervertebral fusion. Many types of spine implants are available for performing spinal fixation, including the Harrington hook and rod, pedicle screws and rods, interbody fusion cages, and sublaminar wires.

Spinal stenosis pain or from impingement of nerve roots in the neural foramina has been treated by laminectomy and foraminotomy. Thereafter, the posterior spine is sometimes reinforced with rod and screw fixation. More recently, surgeons have attempted to relieve spinal stenosis by distracting adjacent spinous processes with a wedge implant. Pain due to instability of the spine has also been treated with dynamic stabilization of the posterior spine, using elastic bands that connect pedicles of adjacent vertebrae.

A number of spinal deformities exist where the spine is abnormally twisted and or curved. Scoliosis is typically considered an abnormal lateral curvature of the vertebral column.

Correction of scoliosis has been attempted a number of ways. Typically correction is followed by fusion. For example, a Harrington rod has been used where a compressing or distracting rod is attached above and below a curved arch of the deformity. The spine is stretched longitudinally to straighten the spine as the rod is lengthened. The spine is then fused. The correction force in this device and in similar devices is a distraction force that may have several drawbacks including possible spinal cord damage, as well as the high loading on the upper and lower attachment sites. Nowadays, segmental hook and screw fixation exists for providing distraction and derotating corrective forces.

A Luque device has been used where the spine is wired to a rod at multiple fixation points along the rod and pulls the spine to the rod. The spine is pulled to the rod with a wire and the spine is then fused. Anterior procedures also exist in the form of fusion via rod and screw fixation systems and newer technology involving staples across the disc space that purport to correct the deformity without requiring fusion. The corrective force is derotation with or without compression.

SUMMARY OF THE INVENTION

In accordance with one embodiment, a system for correcting a spinal deformity is described. The system for correcting a spinal deformity comprises at least one implant configured to be fixed to a first side of a vertebra. The system further comprises a rod adapted to extend generally along an axis parallel to an axis of the spine, on a second side of the vertebra, and at least one adjustment member coupled to the rod. The system further comprises at least one force directing member adapted to extend between the implant and the adjustment member. The force directing member is retractable toward and extendible from the adjustment member. In one aspect of the embodiment, the system comprises a plurality of implants and a plurality of force directing members. In such an aspect, the system can comprise a plurality of adjustment members, and each of the force directing members can extend between one of the implants and one of the adjustment members. In one aspect of the embodiment, the force directing member is a cable. In a further aspect, the adjustment member comprises a reel. In such an aspect, the system for correcting a spinal deformity may comprise a housing at least partially surrounding the reel. In the same aspect, the reel may be rotatable on an axis normal to the axis of the rod. Alternatively, the reel may be rotatable on an axis generally in line with the axis of the rod. Further in the same aspect, the system may comprise at least one gear configured to turn the reel. In another aspect of the embodiment, the system comprises an implantable motor configured to drive the at least one adjustment member. In such an aspect, the motor can comprise a stepper motor. Additionally, the system can comprise an implantable power source configured to supply power to the motor. In another aspect of the embodiment, the implants each comprise a first portion configured for fixation to a pedicle on the first side of a vertebra and a second portion configured to extend to the second side of the vertebra when the first portion is fixed to the pedicle. In such an aspect, the first portion may be a pedicle screw. In the same aspect, the second portion may be configured to pass through a spinous process of the vertebra. The system may further comprise a load-spreading member configured to spread load applied by the force directing member to the spinous process.

In accordance with another embodiment, a system for correcting a spinal deformity comprises means for establishing a desired orientation of vertebrae, means for applying force to an individual vertebra, means for directing force to the force applying means, and means for retracting the force directing means toward the orientation establishing means. The means for directing force extends between the force applying means and the orientation establishing means. In one aspect of the embodiment, the system further comprises means for extending the force directing means away from the orientation establishing means.

In accordance with yet another embodiment, a system for correcting a spinal deformity comprises an elongate rod and a plurality of adjustment members coupled to the rod and spaced apart along the rod. The system further comprises a plurality of flexible force-directing members attached to the adjustment member and adapted to be drawn toward the rod by the adjustment member. The system further comprises a plurality of implants. The implants are each configured to connect to a vertebra of a spine and to be a force directing member, allowing a plurality of vertebrae to each be drawn by a said force directing member and a said adjustment member toward the rod.

In accordance with a further embodiment, a method of correcting a spinal deformity is described. The method comprises affixing an implant to a first side of a vertebra and positioning a rod on a second side of the vertebra so that the rod extends generally parallel to an axis of the spine. The method further comprises providing at least one adjustment member positioned along the rod and positioning at least one force directing member so that it extends between the adjustment member and the implant. The method further comprises applying a force to the at least one force directing member with the adjustment member, thereby moving the vertebra toward the rod. In one aspect of the embodiment, the force is applied percutaneously. In another aspect, the force is applied non-invasively. In such an aspect, the force can be applied using HF energy. In such an aspect, the force can be applied using an implanted power source. In such an aspect, the force can be applied by an implanted motor. In one aspect of the embodiment, the method comprises affixing a plurality of the implants to the first side of a plurality of vertebrae and providing a plurality of the adjustment members positioned along the rod. In such an aspect, the method further comprises positioning a plurality of the force directing members between adjustment members and implants, and then applying a force to each of the plurality of force directing members. In such an aspect, a different force may be applied to each force directing member. In another aspect, the force directing member is a wire. In yet another aspect, the force directing member is a cable. In a further aspect, the adjustment member comprises a reel. In such an aspect, the method can further comprise providing a housing at least partially surrounding the reel. In the same aspect, the reel can be rotatable on an axis normal to the axis of the rod. Alternatively, the reel may be rotatable on an axis generally in line with the axis of the rod. Further in such an aspect, the method may comprise at least one gear configured to turn the reel. In another aspect of the embodiment, the implant comprises a first portion configured for fixation to a pedicle on the first side of a vertebra and a second portion configured to extend to the second side of the vertebra when the first portion is fixed to the pedicle. In such an aspect, the first portion may be a pedicle screw. In the same aspect, the second portion may be configured to pass through a spinous process of the vertebra. The method may further comprise a load-spreading member configured to spread load applied by the force directing member to the spinous process. In a further aspect, the implant is affixed to multiple locations on the vertebra such that applying the force to the force directing member with the adjustment member both moves the vertebra toward the rod and derotates the vertebra.

BRIEF DESCRIPTION OF THE DRAWINGS

The above-mentioned and other features of the invention will now be described with reference to the drawings of various embodiments which are intended to illustrate but not to limit the invention. The drawings contain the following figures.

DETAILED DESCRIPTION OF THE PREFERRED EMBODIMENT

The following description and the accompanying figures, which describe and show certain preferred embodiments, are intended to demonstrate several possible configurations that systems for adjusting anatomical structures can take to include various aspects and features of the invention. The illustrated embodiments are shown correcting a scoliotic curvature of a spine. The illustration of embodiments in this context is not intended to limit the disclosed aspects and features of the invention to the specified embodiments or to usage only in correcting scoliosis. Those of skill in the art will recognize that the disclosed aspects and features of the invention are not limited to any specifically disclosed embodiment, and systems which include one or more of the inventive aspects and features herein described can be designed for use in a variety of applications.

As used herein, the term "vertical" refers to a direction generally in line with, or generally parallel to, a sagittal plane of the body (e.g., generally parallel to the axis of a straightened spine in a standing patient). The terms "transverse" and "horizontal" refer to a direction generally in line with, or generally parallel to, a transverse plane of the body (or a transverse plane of a vertebral body), and normal to a sagittal plane of the body (e.g., running from side to side across the spine of a standing patient).

The preferred embodiments of the present invention advantageously provide improved systems and methods for adjusting or correcting an anatomical structure, such as an abnormally curved spine, in a patient. According to one embodiment, the system includes a rod which can be disposed along a vertical axis on one side of a patient's spine. The system also includes one or more fixation devices or implants that can be disposed on the other side of the patient's spine, each of which can be inserted into, or otherwise attached to, one or more vertebrae. A connector extends between each implant and the rod. Coupled to the rod is at least one adjustment mechanism which is coupled to the connector. Activation of the adjustment mechanism adjusts the length of the connector, allowing adjustment of the forces applied to an individual vertebra through the connector and its associated implant. Some embodiments of the invention thus allow for reversibly adjustable forces to be applied to individual structures, such as individual vertebrae, allowing tensioning and loosening as appropriate. Embodiments of the system can be implanted surgically and then tightened (or loosened) over an extended period of time if desired, with minimally invasive or noninvasive procedures to provide gradual adjustment. Embodiments also provide a system for correcting a deformity of the spine which can be used with or without fusion.

Figure 1:
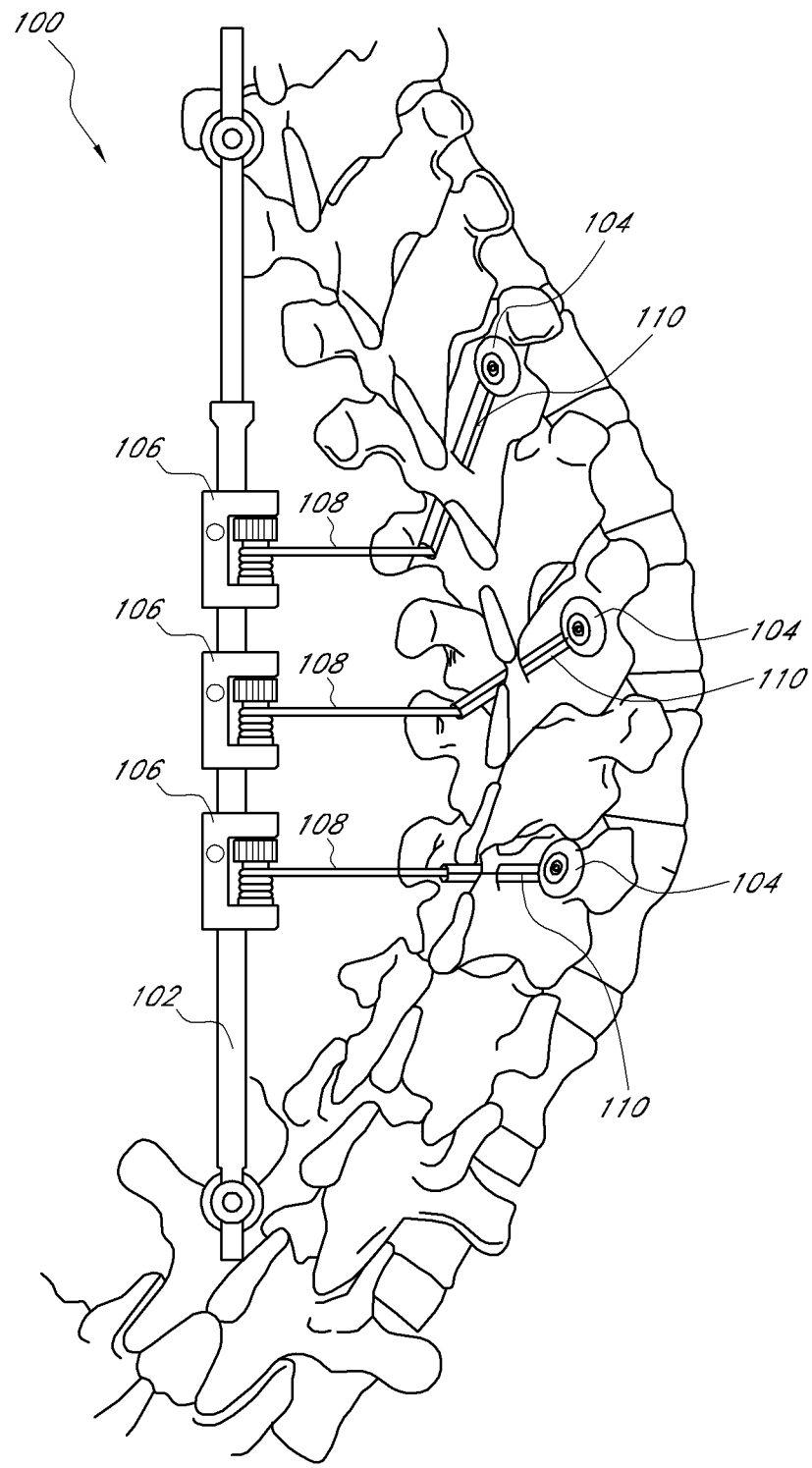
FIG. 1 is a schematic view of a spine deformity correction system in accordance with an embodiment.

With reference now to FIG. 1, a system 100 generally includes a stabilizing rod 102, one or more implants 104, one or more adjustment mechanisms 106, and one or more connectors 108. The rod 102 extends generally vertically and is secured to individual vertebrae at locations above and below the curvature to be corrected. The illustrated rod 102 is attached, according to known methods, to transverse processes on the left side of the spine. Among other functions, the rod serves to establish a desired orientation of the spine. The rod 102 can have an adjustable length, such that its length can adapt to the changing length of the spine as its curvature is straightened. The rod can be a telescoping rod, or the rod can comprise rotatable threaded portions that may be actuated to change overall length of the rod. In addition or in the alternative, the rod 102 can be movable with respect to either or both of the attachment points above and below the curvature of the spine, so as to allow the system 100 to adapt to the lengthening of the spine as the affected vertebrae are translated toward the rod 102. Such a configuration can advantageously prevent buckling in the rod 102 and/or the spinal column as the curvature of the spine is corrected.

Figure 2:
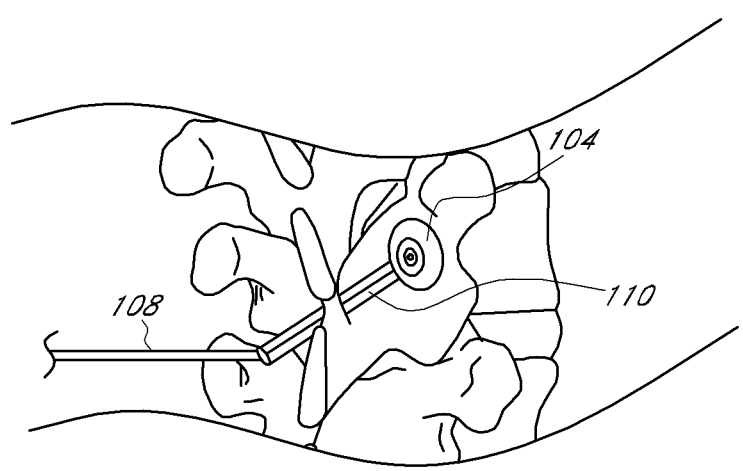
FIG. 2 is an enlarged view of a portion of FIG. 1 showing a fixation device in accordance with the illustrated embodiment.

The implants 104 are shown fixed to individual vertebrae within the curved portion of the spine, on the opposite side of the spine from the rod 102. The implants 104 include transverse portions 110 which extend across the spine, toward the rod 102. As better illustrated in FIG. 2, the transverse portions 110 can pass through the spinous processes of individual vertebrae. Each of the transverse portions 110 is coupled to one of the connectors 108. The connectors 108 extend transversely from the transverse portions 110 of the implants 104 toward the rod 102, and are coupled to the rod 102 via the adjustment mechanisms 106. The connectors 108 are preferably flexible so that they can be used with adjustment mechanisms 106 of a spooling or winding type. Suitable flexible connectors 108 include monofilament polymer materials, multifilament polymer materials (such as or similar to string or rope), multifilament carbon or ceramic fibers, wire, and multi-stranded cable. Stainless steel or titanium wire or rope are some examples of suitable materials. Of course, a wide variety of materials can be used to make the connectors 108. In an embodiment, those materials are preferably biocompatible; indeed, the entire system is preferably made of biocompatible materials.

Figure 3:
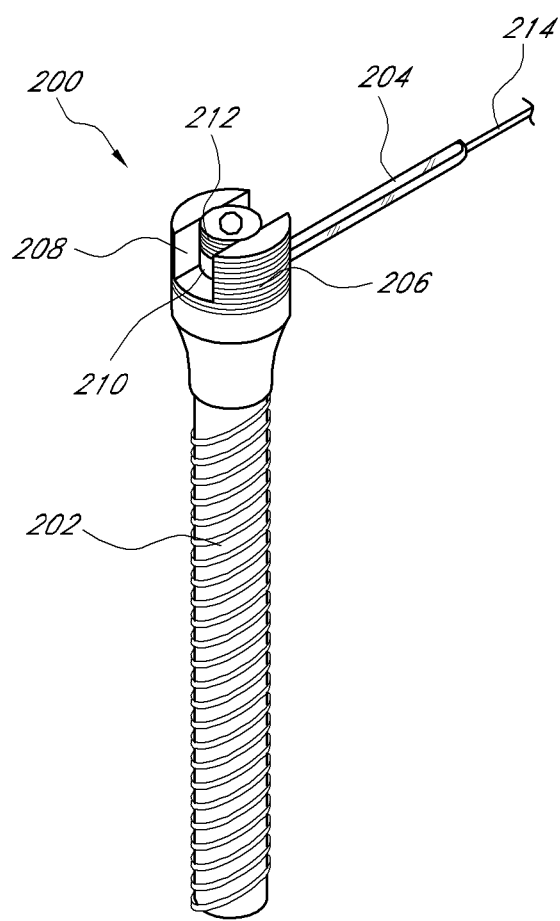
FIG. 3 is a perspective view of a fixation device according to an embodiment.
Figure 4:
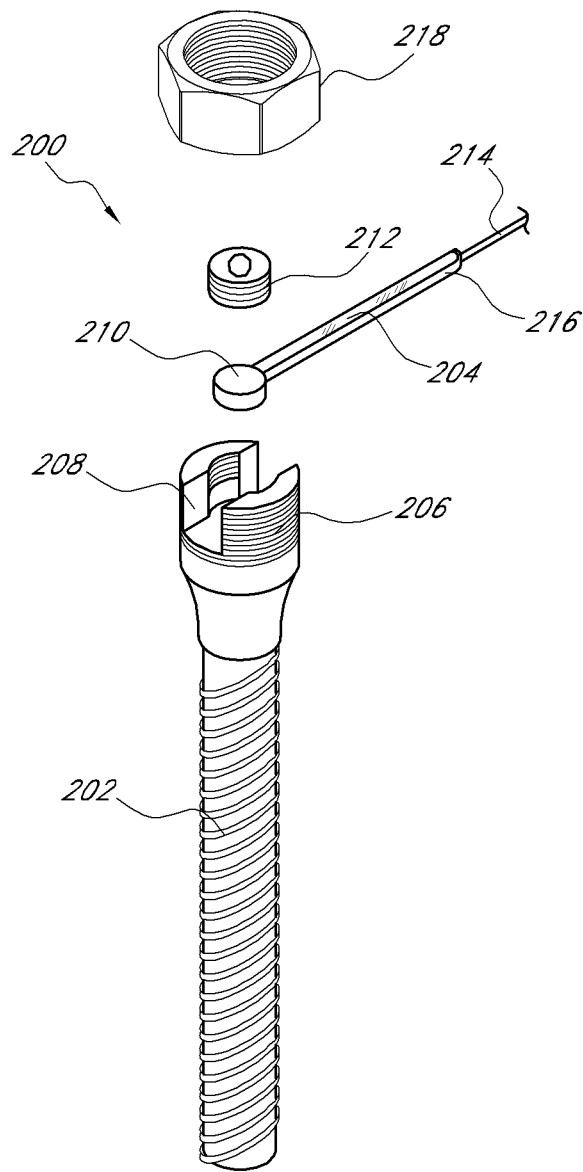
FIG. 4 is an exploded view of the fixation device shown in FIG. 3.

FIGS. 3 and 4 illustrate in detail an implant 200 configured in accordance with an embodiment. The implant 200 includes a fixation portion 202 which is configured to be fixed to a portion of a vertebra, such as a pedicle. The fixation portion 202 can comprise any suitable structure capable of engaging a portion of a vertebra, such as, for example, the illustrated pedicle screw. The implant 200 also includes a transverse portion 204 coupled to the top end 206 of the fixation portion 202. The transverse portion 204 is disposed generally perpendicularly to the fixation portion 202. The fixation portion 202 includes at its top end 206 a slot 208 configured to receive a first end 210 of the transverse portion 204. The slot 208 is sized to receive a set screw 212 which, when engaged in the slot 208 on top of the first end 210 of the transverse portion 204, serves to secure the position of the transverse portion 204 relative to the fixation portion 202. In addition to or instead of the set screw 212, an external nut 218 can be used to provide additional securement of the transverse portion 204 relative to the fixation portion 202. Of course, as will be understood by one of skill in the art, any suitable coupling can be used to join the fixation portion 202 and the transverse portion 204. Further, depending on the particular application, the implant can also have a unitary construction.

Figure 5:
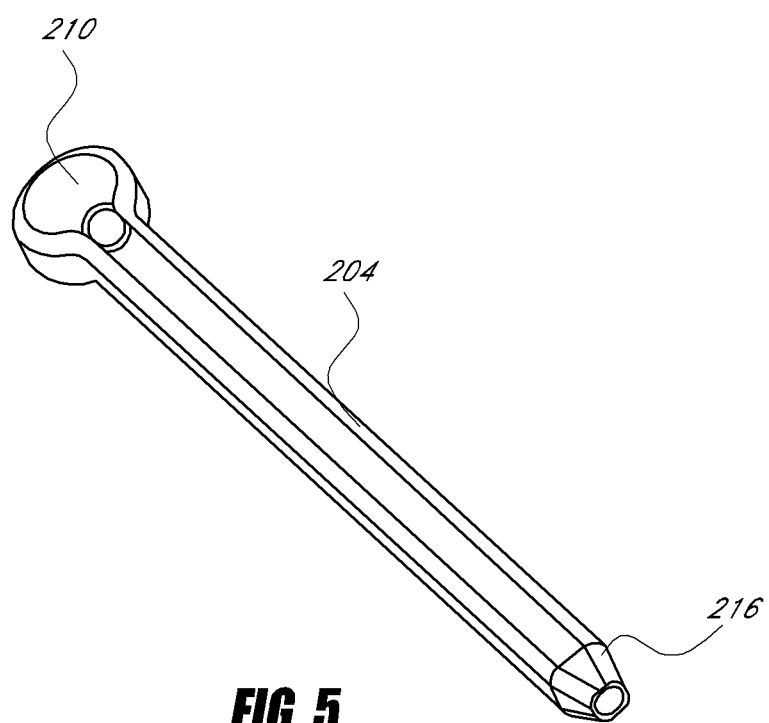
FIG. 5 is a perspective view of the transverse member of the fixation device shown in FIG. 3.

A connector 214 extends from a second end 216 of the transverse portion 204 by an amount sufficient to connect to an adjustment mechanism coupled to a rod, as described herein. The connector 214 can be attached to the first end 210 of the transverse portion 204, extending along the length of and past the second end 216 of the transverse portion 204. Alternatively, the connector 214 can be attached at any other location along the length of the transverse portion 204. The connector 214 may advantageously comprise, for example, a cable or wire, or another material as set forth above, and can be fixed to the transverse portion 204 in any suitable manner, such as by welding or screw fixation. FIG. 5 illustrates the transverse portion 204 in further detail. As shown in the figure, the transverse portion 204 can have a wider, roughly disk-shaped first end 210 so as to engage the receiving slot 208 in the fixation portion 202. Of course, the first end 210 of the transverse portion 204 and the top end 206 of the fixation portion 202 can have any other suitable cooperating configuration so as to guide and engage one another in an appropriate orientation. The transverse portion 204 can also have a hollow construction through which the connector 214 can extend.

Figure 6:
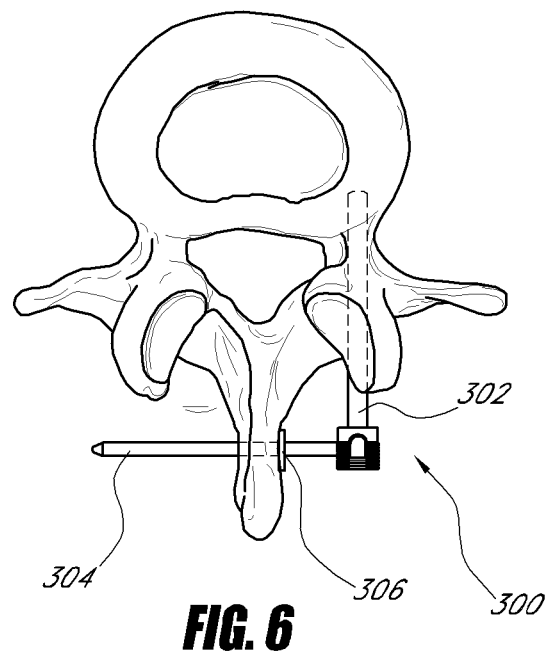
FIG. 6 is a top plan view of a fixation device according to an embodiment, shown implanted in a vertebra.

With reference now to FIG. 6, an implant 300 in accordance with an embodiment is shown fixed to a single vertebra. The implant 300 includes a pedicle screw 302 which is fixed to one side of the illustrated vertebra. A transverse member 304 is advantageously coupled to the head of the pedicle screw 302 and extends through the spinous process of the illustrated vertebra. A load-spreading member 306 can be provided which encircles, or partially encircles the transverse member 304 at the point of contact between the spinous process and the transverse member 304, contralateral to the adjustment mechanism and rod (not shown in FIG. 6).

Figure 7A:
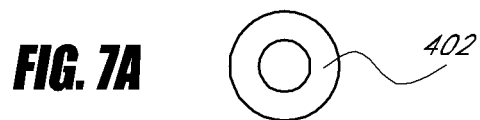
FIGS. 7A through 7C show plan views of various load-spreading members that can be used with embodiments of the invention.
Figure 7B:
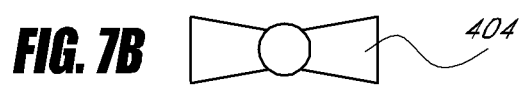
Figure 7C:
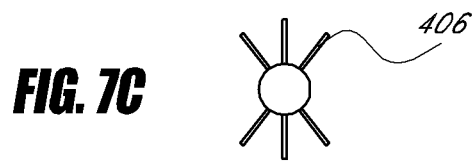

FIGS. 7A through 7C illustrate various configurations of load-spreading elements according to various embodiments. Element 402 has an annular configuration configured to spread loads evenly about the point of contact with the spinous process. Element 404 includes two wings extending from a ring configured to encircle the transverse member. Element 406 includes tentacles extending from a ring. Configurations such as these can also be used to distribute loads to the lamina, in addition to spreading loads across a larger surface area of the spinous process. Of course, a load-spreading element can have any other configuration suitable for reducing the concentration of force applied to the spinous process by a transverse member extending therethrough, distributing the forces to other portions of the vertebra (for example, to the lamina), and/or for anchoring the transverse member to the spinous process. In addition, the side of the load-spreading elements that contact bone can include such features as barbs, fins, pins, or other similar structure to achieve secure attachment of the extensions to the vertebral bone.

Although the illustrated embodiments generally include implants having transverse members which extend through the spinous process of a vertebra, and thus show examples of implants which are fixed at multiple locations on an individual vertebra, embodiments of the invention also include implants which are fixed to only a single location on an individual vertebra. For example, an implant according to an embodiment can include a transverse member configured to extend between spinous processes of adjacent vertebra. In such an embodiment, the transverse member can optionally be anchored to one or both of the adjacent spinous processes via a cable, tether, clasp, clamp, screw, hinge, or other suitable means. In addition, although the illustrated embodiments generally show each implant fixed to a single vertebra, embodiments can also include one or more implants configured to be fixed to multiple vertebrae. Additional examples of implants, as well as rods, which may be used with embodiments of the invention are set forth in copending U.S. application Ser. No. 11/196,952, the disclosure of which is hereby incorporated in its entirety. One advantage of multiple-point fixation is the ability to provide not only translational force to the vertebra through the implant, but also rotational force. The amount of rotational force will depend in part on the distance between the axis of the vertebra and the point of attachment of the connector 108 to the implant 104. This disclosure contemplates selecting or moving that point of attachment to achieve any desired rotational force, as well as a desired translational force.

Figure 8:
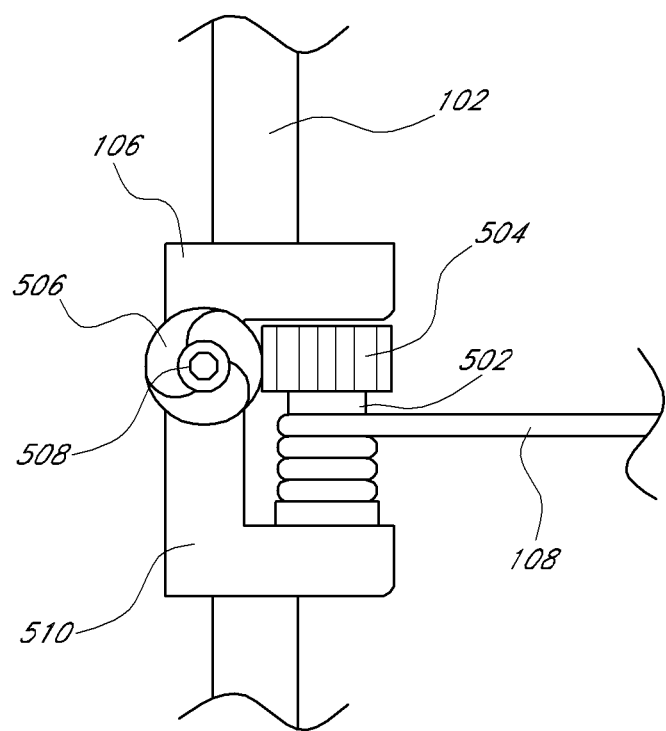
FIG. 8 is an enlarged view of a portion of FIG. 1 showing an adjustment mechanism in accordance with the illustrated embodiment.

With reference now to FIG. 8 a particular adjustment mechanism 106 shown in FIG. 1 is illustrated in further detail. The adjustment mechanism 106 may advantageously include a reel 502, a circumferential gear 504 surrounding the reel 502, and a vertical gear 506 in contact with the circumferential gear 504. The connector 108 is preferably attached to or engaged by the reel 502. Actuation of the vertical gear 506 via screw head 508 turns the circumferential gear 504, which turns the reel 502, thus winding (or unwinding, depending on the direction in which the reel 502 is turned) the connector 108 about the reel 502. Tightening of the reel 502 draws the connector 108 in toward the adjustment mechanism 106, thus pulling the associated implant 104 (not shown in FIG. 8) toward the adjustment mechanism. The reel 502 and the gears 504, 506 are housed in a clamp 510. The adjustment mechanism 106 can be immovably fixed to the rod 102 or can be movable with respect to the rod 102. A movable adjustment mechanism 106 provides advantages, for example, as the spine straightens and thus lengthens, so that the adjustment mechanisms 106 can be moved to accommodate the relative movement of the spine in comparison to the rod 102. A movable adjustment mechanism 106 also tends to move to the point directly across from the implant 104, which is the position creating the least amount of tension in the connector 108 and which is also the ideal position for correction.

Figure 9:
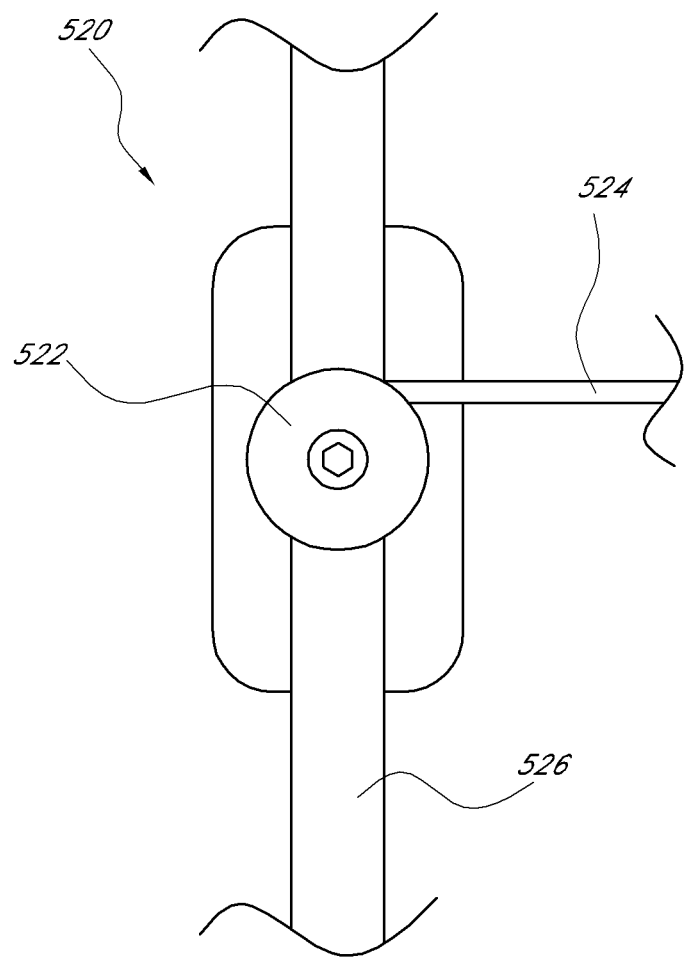
FIGS. 9 through 13 show schematic views of adjustment mechanisms according to various embodiments.
Figure 10:
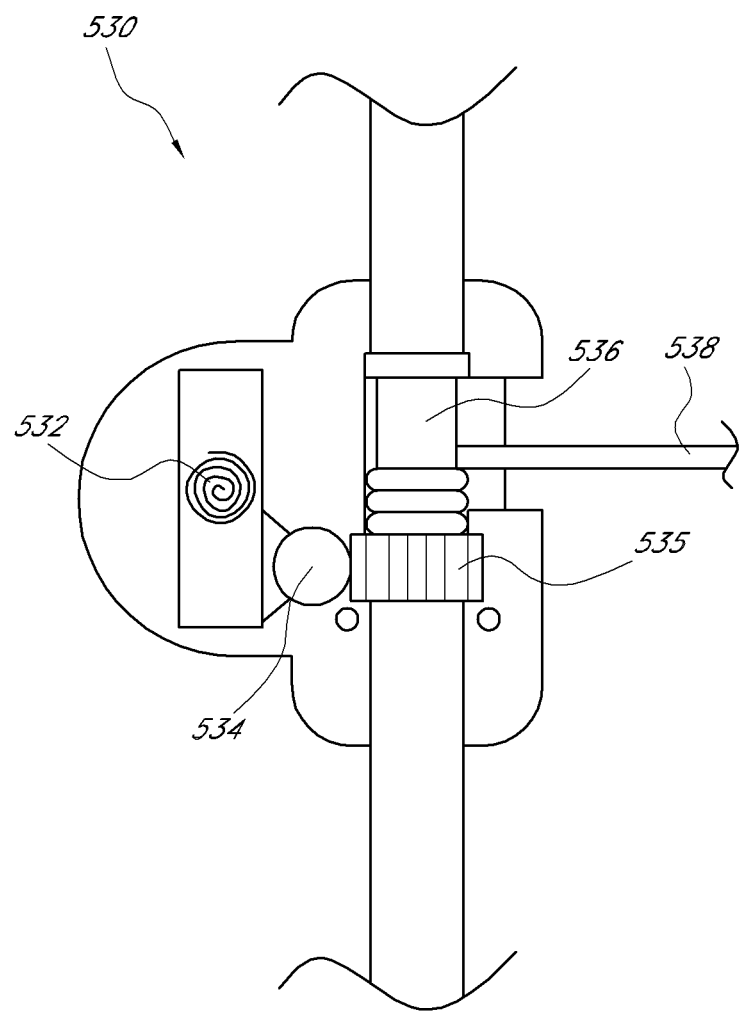
Figure 11:
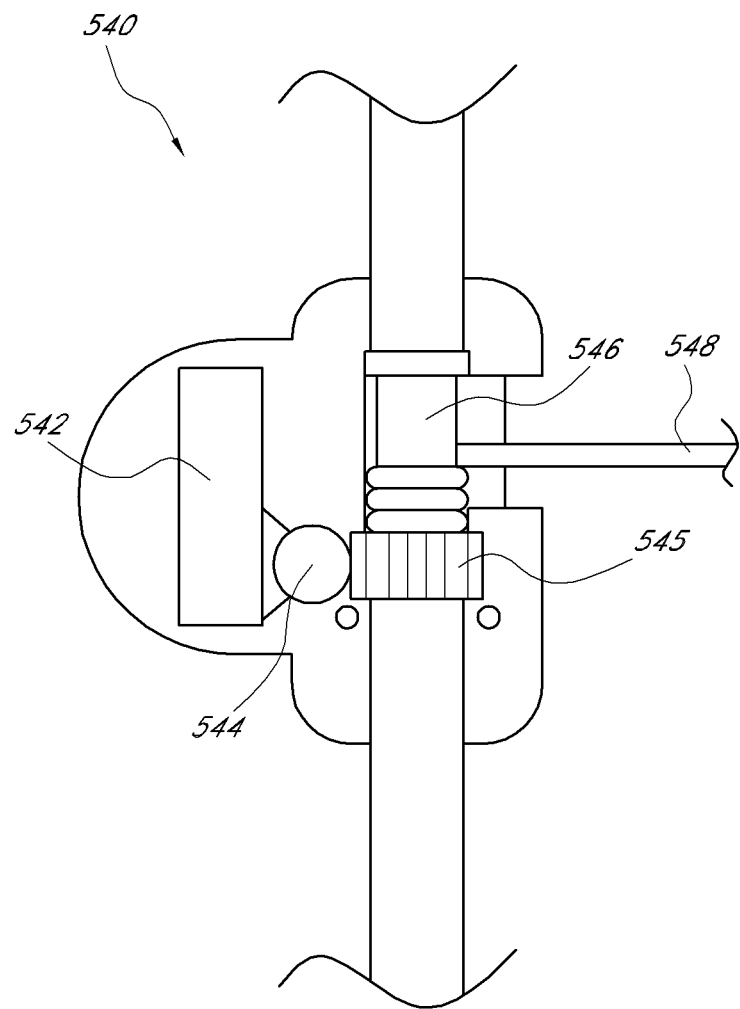
Figure 12:
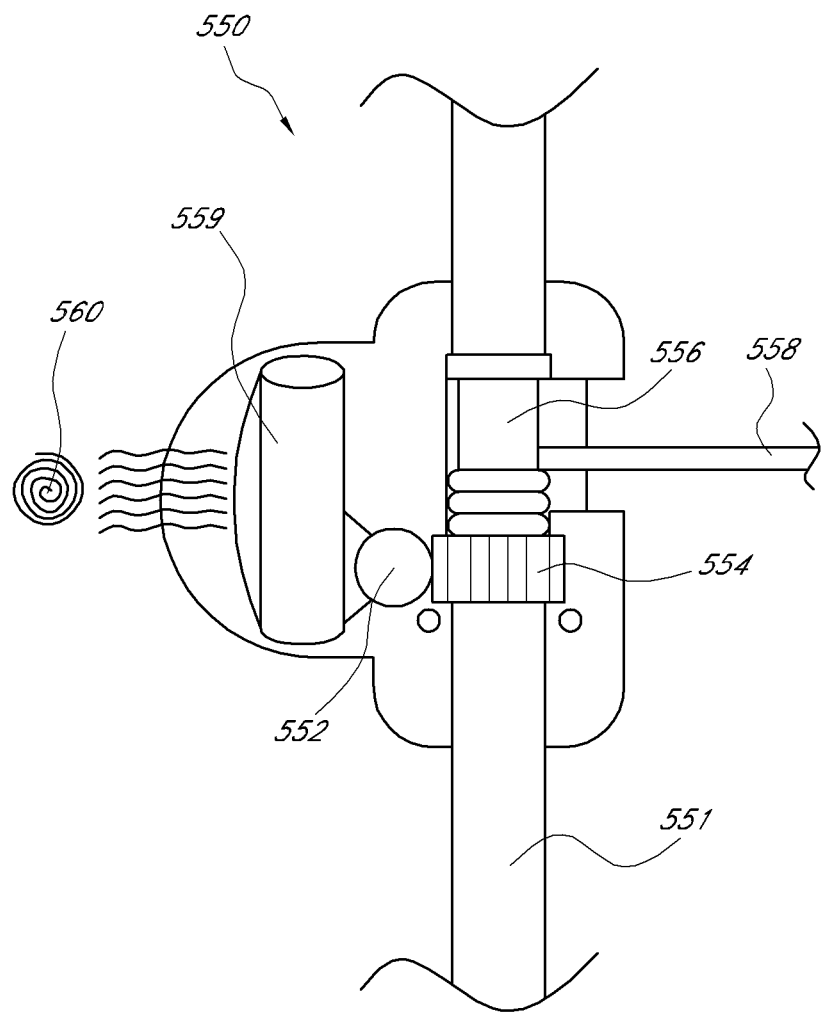
Figure 13:
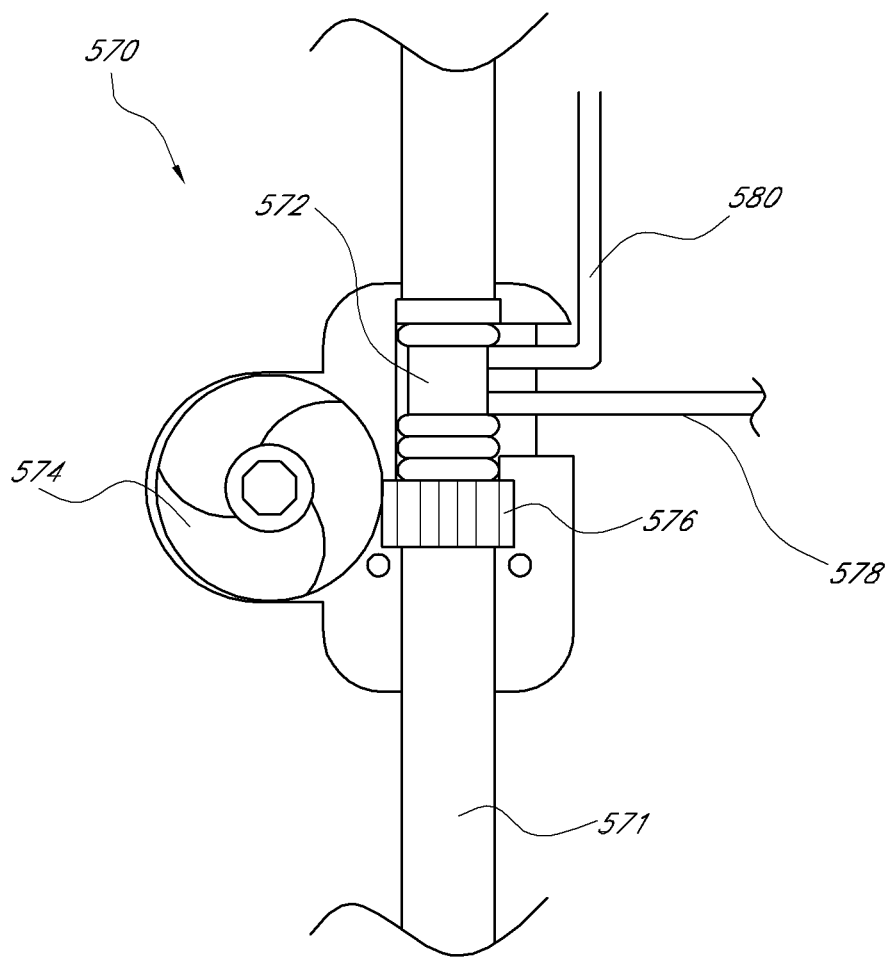

An adjustment mechanism can be configured in any manner suitable for retracting and letting out a connector. FIGS. 9 through 13 show examples of adjustment mechanisms according to further embodiments. FIG. 9 shows an adjustment mechanism 520 comprising only a single reel or gear 522, around which a connector 524 is wound. The gear 522 is disposed along on an axis normal to the axis of the rod 526. The gear 522 can be directly actuated to tension or loosen the connector 524. FIG. 10 shows an adjustment mechanism 530 according to a further embodiment. The mechanism 530 includes a spring 532 configured to actuate a vertical gear 534. The vertical gear 534 contacts a circumferential gear 535 on a reel 536 around which a connector 538 is wound. In such an embodiment, the spring 532 can exert gradual forces on the connector 538 (and thus, on an implant to which the connector 538 is attached) without the need for puncturing the patient's skin. FIG. 11 shows an adjustment mechanism 540 according to another embodiment. The mechanism 540 includes an implantable power supply 542 configured to actuate a motor 544. The motor 544 drives a gear 545 on a reel 546 around which a connector 548 is wound. In such an embodiment, the motor 544 can be configured to exert gradual forces on the connector 548 (and thus, on an implant to which the connector 548 is attached) without the need for puncturing the patient's skin after the initial implantation of the system. For example, the motor 544 can be configured to draw in the connector 548 at a predetermined rate (e.g., 3 mm per day). In some embodiments, the motor 544 can be a stepper motor configured to draw in the connector 548 in incremental amounts over time. In other embodiments, the motor 544 can be configured to exert a predetermined amount of tension on the connector 548. Such embodiments can include one or more sensors, controllers, and related circuitry configured to measure the amount of tension on the connector 548 and adjust the tension applied by the motor 544 accordingly. Such embodiments can be configured to time-average the amount of tension on the connector 548 to allow for variation in tension caused by movement of the patient. In addition, such embodiments can be configured to maintain varying levels of tension on the connector 548 at different periods throughout the day, for example maintaining a lower level of tension during waking hours and a higher level of tension during sleeping hours. Further, in embodiments comprising multiple adjustment mechanisms configured to apply tension to multiple different vertebrae through multiple connectors, each adjustment mechanism can be configured to maintain a different level of tension on its associated connector, depending on the needs of the particular application. FIG. 12 shows an adjustment mechanism 550 according to a still further embodiment. The mechanism 550 is coupled to a rod 551, and includes a first gear 552 configured to turn a second gear 554. The second gear 554 contacts a reel 556, to which a connector 558 is attached. Turning of the second gear 554 causes the reel 556 to rotate, thereby pulling in (or letting out) the connector 558 toward (or from) the rod 551. The first gear 552 is driven by an electric motor 559, which is configured for remote actuation by an external HF transmission coil 560. Such a configuration allows for post-implantation adjustment of the connector 558 without puncturing the patient's skin. Any suitable external energy source can be used in an embodiment configured for remote actuation, such as, for example, RF energy, HF energy, or magnetic energy. FIG. 13 illustrates an adjustment mechanism 570, according to a still further embodiment, coupled to a rod 571. The mechanism 570 includes a reel 572 which is actuated by first and second gears 574, 576. The reel 572 is attached to a first connector 578, which extends generally transversely to an implant on the other side of the spine. Also connected to the reel 572 is a second connector 580, which extends generally parallel to the rod 571. The second connector 580 is connected to a second adjustment mechanism (not shown) and configured so that tightening of the mechanism 570 results in tightening of the second adjustment mechanism as well. Of course, additional adjustment mechanisms can be coupled to such a system so that a multiple-implant system can be adjusted using a single adjustment point.

In the various illustrated embodiments, the adjustment mechanism 106 is shown to be situated along the rod so that the connector 108 extends generally orthogonal to the rod toward the vertebra on which the implant 104 is located. Although this is a preferred embodiment, it is also contemplated that the adjustment mechanism 106 can be located along the rod 102 so that the angle between the axis of the rod 102 and the connector 108 is other than 90 degrees, e.g., 45 degrees, 60 degrees, 75 degrees, or other non-right-angles. Alternatively, instead of locating the adjustment mechanism(s) 106 along the rod 102 adjacent to (or opposite) the vertebra to be moved, they could be located more remotely, e.g., at an end of the rod 102. In that configuration, the connector could still extend from the implant 104 to the rod 102 at a desired angle, e.g., generally orthogonal to the rod 102, but could then change direction (e.g., by passing over a pulley or through a hole in the rod, not shown) and then extend parallel to or coaxial with the rod, alongside the rod or inside the rod, to the adjustment mechanism(s) 106.

Figure 14:
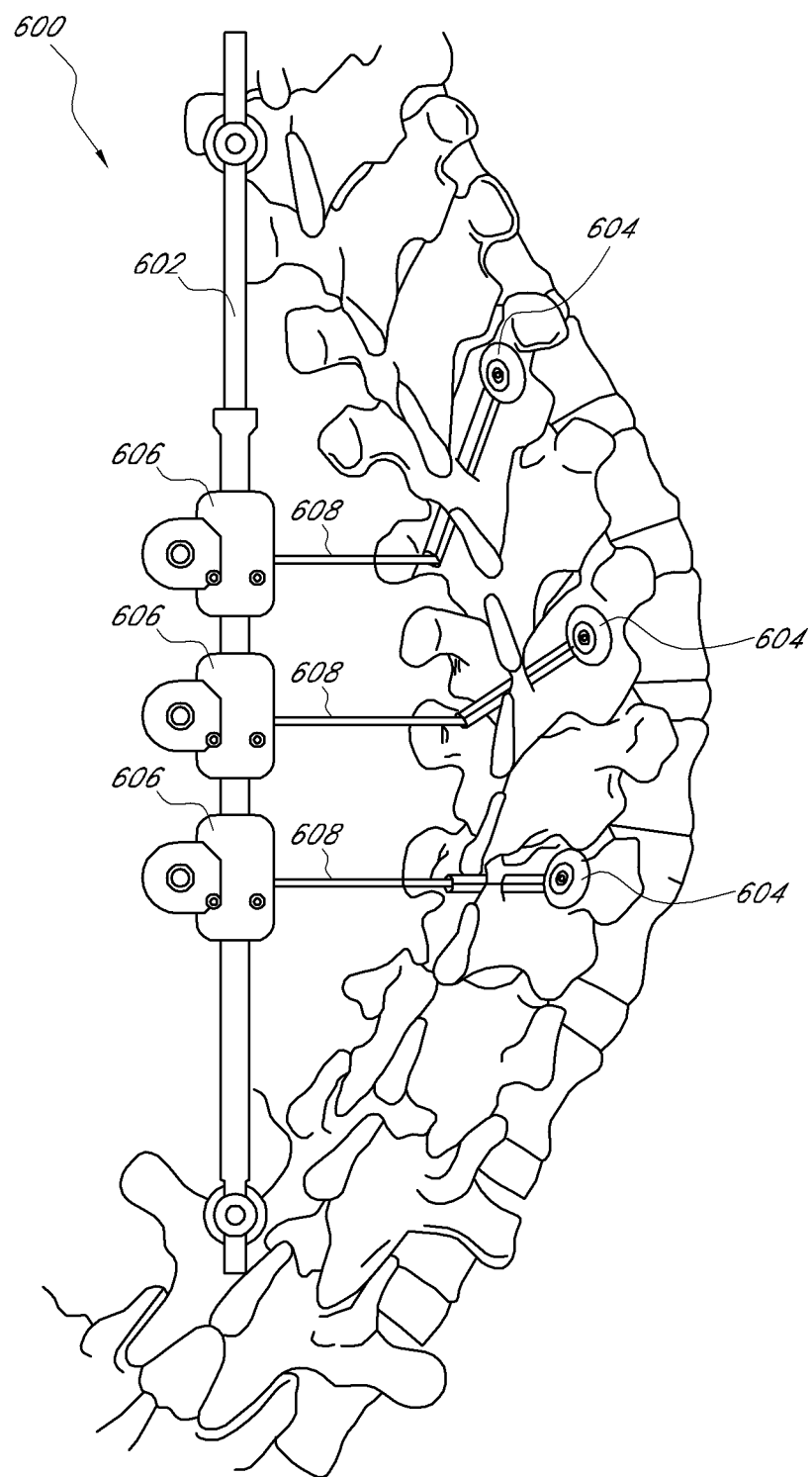
FIG. 14 is a schematic view of a spine deformity correction system in accordance with a further embodiment.
Figure 15:
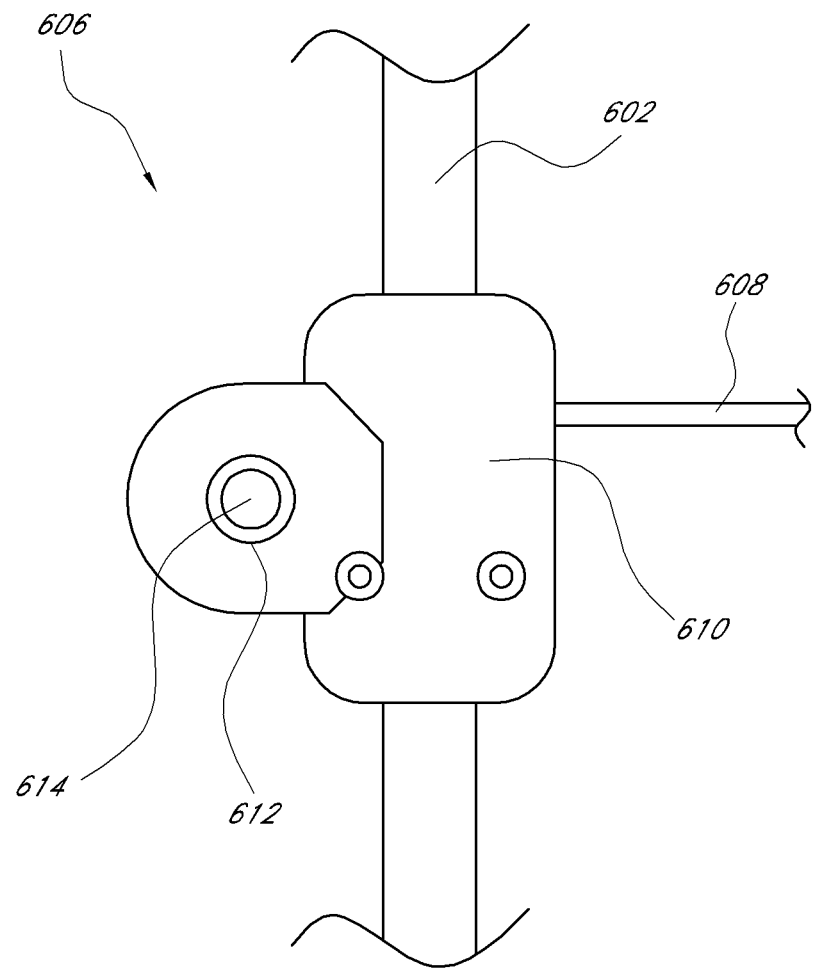
FIG. 15 is an enlarged view of a portion of FIG. 14 showing an adjustment mechanism in accordance with the illustrated embodiment.

With reference now to FIG. 14, a system 600 according to another embodiment is illustrated. The system 600 includes a stabilizing rod 602, one or more implants 604, one or more adjustment mechanisms 606, and one or more connectors 608. The implants 604 are shown attached to alternate vertebrae. Depending on the particular needs of the application, implants 604 can be fixed to all the vertebrae in a curved portion of a spine, or only certain selected vertebrae. FIG. 15 shows an enlarged view of one of the adjustment mechanisms 606. The adjustment mechanism 606 includes a housing 610 which surrounds a gear/reel mechanism (not visible in FIG. 15) as described herein. The housing 610 includes an opening 612 configured to expose a screw head 614 configured to actuate the gear/reel mechanism. Such a configuration allows for actuation of the gear/reel mechanism 606 while separating the gear/reel mechanism and surrounding body tissues.

Embodiments also include methods of correcting a spinal deformity. Note that the following method description relates to some of the contemplated surgical methods, but it should not be implied that all of the recited method steps are mandatory or that they must be performed in the identical manner specified. Instead, this disclosure is exemplary in nature. In some embodiments, individual vertebrae are targeted based on a pre-operative plan for correcting an abnormal curvature a patient's spine (such as a scoliotic curvature of a patient's spine). Pre-operative planning can involve review of x-rays or CT scans, as well as physical examination of the patient. Once the targeted vertebrae are identified, implants are surgically fixed to each of the targeted vertebrae. Fixing each implant can involve fixing a first portion of the implant into a pedicle of a vertebra on one side of the patient's spine, inserting a second portion of the implant through a spinous process of the same or different vertebra, and coupling the first and second portions together. A vertically extending rod is surgically fixed to the other side of the patient's spine so as to establish a desired orientation of the targeted vertebrae. Adjustment mechanisms of the same number as the implants (that is, the same number as the targeted vertebrae) are movably or immovably fixed to the rod. Connectors are positioned between each adjustment member and its corresponding implant. The adjustment mechanisms are then actuated to pull the connectors (and thus the targeted vertebrae) toward the rod. The adjustment mechanisms allow for both tightening and loosening of the connectors and, thus, the application of force is reversible. The adjustment mechanisms can be tightened or loosened as deemed appropriate by the practitioner and then locked with a locking mechanism such as a set screw. In embodiments having implants coupled to multiple points on each vertebra, applying tension to the connectors also exerts rotational forces on the targeted vertebrae, thus derotating the spine as the vertebrae are pulled toward the rod.

Once the initial adjustments are made to the adjustment mechanisms, the surgical site is closed using standard surgical procedures. The patient is then examined periodically (for example, every 3 to 6 months) and additional adjustments are made when appropriate. Depending on the configuration of the adjustment mechanisms, post-implantation adjustment can be made via a percutaneous puncture allowing the passing of a driver to actuate each adjustment mechanism. In embodiments including adjustment mechanisms configured for remote actuation, adjustments can be made without the need for puncturing the patient's skin. Adjustments can be different at each level or adjustment mechanism, depending on the particular anatomy to be adjusted, and different forces or force vectors can be applied to different vertebrae or sections of the spine. Both the curvature and the mal-rotation of the scoliotic spine can thus be corrected over multiple serial adjustments of the adjustment mechanisms. If desired, the system may be explanted after the deformity of the spine is eliminated or reduced to a clinically acceptable position.

Figure 16:
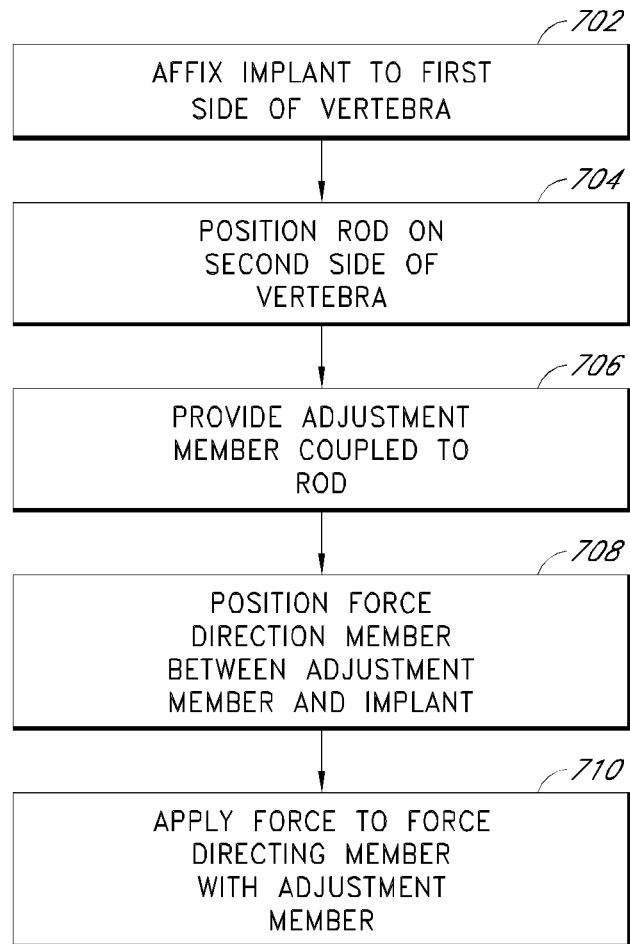
FIG. 16 is a process diagram illustrating a method of correcting a spinal deformity, according to a further embodiment.

A method of correcting a spinal deformity is illustrated in FIG. 16. At step 702, an implant is affixed to a first side of a vertebra. At step 704, a rod is positioned on a second side of the vertebra so that the rod extends between the adjustment member and the implant. At step 706, an adjustment member is provided which is coupled to the rod. At step 708, a force directing member is positioned so that it extends between the adjustment member and the implant. At step 710, a force is applied to the force directing member with the adjustment member, thereby moving the vertebra toward the rod.

Embodiments of the invention can be used with or without fusion of vertebrae. For example, according to embodiments, some vertebrae of the spine may be fused according to known procedures using screws, hooks and/or rod systems following initial or subsequent adjustments or after explanation. Alternatively, some or all vertebrae may be left non-fused.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present system has been described in the context of particularly preferred embodiments, the skilled artisan will appreciate, in view of the present disclosure, that certain advantages, features and aspects of the system may be realized in a variety of other applications. For example, while particularly useful in the illustrated scoliosis-correcting application, the skilled artisan can readily adopt the principles and advantages described herein to a variety of other applications, including and without limitation, ameliorating or correcting other spinal conditions such as kyphosis, spondylolisthesis, laxity of spinal motion segments, and other disorders of alignment or loading of the spine.

In addition, as will be understood by one of skill in the art, one or more adjustment mechanisms according to embodiments can be used to adjust tension on anatomical structures other than spinal structures. For example, embodiments of the invention can be configured and used to adjust the tension, laxity, or distance between an anchor structure and an anatomical structure. Examples of such embodiments include providing an adjustable ligament between the femur and tibia of the leg, for example to correct a torn cruciate ligament; providing an adjustable sling between the pelvis or pubis and the bladder or urethra for the treatment of urinary incontinence; providing an adjustable attachment between a bone (such as the pelvis) and the uterus for the treatment of uterine prolapse; providing an adjustable attachment between the mandible or hyoid bone and the tongue or other upper airway structure for the treatment of snoring or obstructive sleep apnea; and providing an adjustable lifting mechanism between a cranial bone and soft tissue of the face to enable an adjustable face lift or eye lift.

Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above.

What is claimed is:

1. A system for correcting a spinal deformity, the system comprising:
   a reel;
   a flexible connector;
   an adjustment mechanism configured to adjust tension of the flexible connector;
   a first implant adapted to transmit tensile force from the flexible connector to bone; and
   a second implant to which the adjustment mechanism is connected,
   wherein the adjustment mechanism is movable with respect to an elongate element connected to the second implant, and
   wherein the adjustment mechanism includes a drive mechanism housed within a clamp.

2. The system of claim 1, wherein the first implant is adapted to transmit tensile force from the flexible connector to the bone by anchoring the flexible connector to the bone.

3. The system of claim 1, wherein the flexible connector is a cable or a wire.

4. The system of claim 1, wherein the drive mechanism is configured to rotate the reel.

5. The system of claim 4, wherein the drive mechanism includes a gear transmission configured to apply torque to the reel.

6. The system of claim 1, wherein the second implant is a fastener having a shank extending along a shank axis and the reel is rotatable about a winding axis that is transverse to the shank axis.

7. The system of claim 1, wherein the elongate element is cylindrical in shape.

8. The system of claim 1, configured to correct a curvature of a spine including a first vertebra in which the first implant is implanted and a second vertebra in which the second implant is implanted.

9. The system of claim 1, wherein the adjustment mechanism includes the reel.

10. The system of claim 1, wherein the adjustment mechanism is releasably connected to the second implant.

11. A system for correcting a spinal deformity, the system comprising:
    a reel;
    a flexible connector;
    an adjustment mechanism configured to adjust tension of the flexible connector;
    a first implant adapted to transmit tensile force from the flexible connector to bone; and
    a second implant to which the adjustment mechanism is connected,
    wherein the adjustment mechanism is actuated using a screw head, and
    wherein the adjustment mechanism includes a drive mechanism housed within a clamp.

12. The system of claim 11, wherein the flexible connector is a cable or a wire.

13. The system of claim 11, wherein the drive mechanism is configured to rotate the reel.

14. The system of claim 13, wherein the drive mechanism includes a gear transmission configured to apply torque to the reel.

15. The system of claim 11, wherein the second implant is a fastener having a shank extending along a shank axis and the reel is rotatable about a winding axis that is transverse to the shank axis.

16. The system of claim 11, comprising an elongate element connected to the second implant.

17. The system of claim 11, wherein the adjustment mechanism includes the reel.

18. The system of claim 11, wherein the adjustment mechanism is connected to the second implant so that a location of the adjustment mechanism relative to the second implant is fixed.

19. The system of claim 11, wherein the adjustment mechanism is releasably connected to the second implant.

20. A system for correcting a spinal deformity, the system comprising:
    a reel;
    a flexible connector;
    an adjustment mechanism configured to adjust tension of the flexible connector;
    a first implant adapted to transmit tensile force from the flexible connector to bone; and a second implant to which the adjustment mechanism is connected,
wherein the adjustment mechanism includes a drive mechanism housed within a clamp.

21. The system of claim 20, wherein the flexible connector is a cable or a wire.

22. The system of claim 20, wherein the drive mechanism includes a gear transmission configured to apply torque to the reel.

23. The system of claim 20, comprising an elongate element connected to the second implant.

24. The system of claim 20, wherein the adjustment mechanism includes the reel.

25. The system of claim 20, wherein the adjustment mechanism is connected to the second implant so that a location of the adjustment mechanism relative to the second implant is fixed.

26. The system of claim 20, wherein the adjustment mechanism is releasably connected to the second implant.

* * * * *